(12) United States Patent
Zehavi et al.

(10) Patent No.: US 12,310,666 B2
(45) Date of Patent: May 27, 2025

(54) SYSTEMS, METHODS, AND DEVICES FOR PERFORMING A SURGICAL PROCEDURE USING A VIRTUAL GUIDE

(71) Applicant: Mazor Robotics Ltd., Caesarea (IL)

(72) Inventors: Eliyahu Zehavi, Tel Aviv (IL); Yonatan Ushpizin, Glil Yam (IL); Ido Zucker, Tel Aviv (IL); Avraham Turgeman, Beer Yaakov (IL); Elad Rotman, Netanya (IL); Adi Ess, Ramat Gan (IL)

(73) Assignee: Mazor Robotics Ltd., Caesarea (IL)

( * ) Notice: Subject to any disclaimer, the term of this patent is extended or adjusted under 35 U.S.C. 154(b) by 66 days.

(21) Appl. No.: 17/528,063

(22) Filed: Nov. 16, 2021

(65) Prior Publication Data
US 2023/0149082 A1    May 18, 2023

(51) Int. Cl.
*A61B 34/10*    (2016.01)
*A61B 34/20*    (2016.01)
*A61B 90/00*    (2016.01)

(52) U.S. Cl.
CPC .............. *A61B 34/10* (2016.02); *A61B 34/20* (2016.02); *A61B 90/37* (2016.02); *A61B 90/39* (2016.02); *A61B 2034/102* (2016.02); *A61B 2090/363* (2016.02); *A61B 2090/365* (2016.02)

(58) Field of Classification Search
CPC ......... A61B 34/10; A61B 34/20; A61B 90/37; A61B 90/39; A61B 2034/102; A61B 2090/363; A61B 2090/365
See application file for complete search history.

(56) References Cited

U.S. PATENT DOCUMENTS

| | | |
|---|---|---|
| 2018/0082480 A1* | 3/2018 | White .................... A61B 90/94 |
| 2019/0254753 A1 | 8/2019 | Johnson et al. |
| 2019/0380792 A1* | 12/2019 | Poltaretskyi ....... A61B 17/1659 |
| 2020/0069373 A1* | 3/2020 | Yu .......................... A61B 34/74 |
| 2021/0267691 A1 | 9/2021 | Lang |

* cited by examiner

*Primary Examiner* — Timothy A Musselman
(74) *Attorney, Agent, or Firm* — Sheridan Ross P.C.

(57) ABSTRACT

Systems, methods and devices for performing a surgical procedure using a virtual guide are provided. The system may include a display configured to display an augmented image in an environment. A surgical landmark may be tracked and a parameter of the surgical landmark may be determined. A virtual guide for presentation within the augmented image may be generated and the display may present the virtual guide within the augmented image.

20 Claims, 5 Drawing Sheets

SYSTEMS, METHODS, AND DEVICES FOR PERFORMING A SURGICAL PROCEDURE USING A VIRTUAL GUIDE

BACKGROUND

The present disclosure is generally directed to performing a surgical procedure, and relates more particularly to performing a surgical procedure using a virtual guide.

Displays providing information about a surgical procedure may assist a surgeon or other medical provider in carrying out the surgical procedure. The information provided may include positioning of a patient. Patient anatomy can change over time, particularly following placement of a medical implant in the patient anatomy or after a surgical step is performed to move one or more anatomical elements.

BRIEF SUMMARY

Example aspects of the present disclosure include:

A system for performing a surgical procedure using a virtual guide according to at least one embodiment of the present disclosure comprises a display configured to display an augmented image in an environment; a processor; and a memory storing data for processing by the processor, the data, when processed, causes the processor to: track a surgical landmark; determine a parameter of the surgical landmark; generate a virtual guide for presentation within the augmented image based on the parameter of the surgical landmark; and cause the display to present the virtual guide within the augmented image.

Any of the aspects herein, wherein the virtual guide is related to minimizing at least one of a force and a pressure applied to the surgical landmark.

Any of the aspects herein, wherein the surgical landmark comprises at least one of an anatomical element, an implant, and a marker.

Any of the aspects herein, wherein the parameter comprises at least one of an angle, a pose, a position, an orientation, a size, a trajectory, and a shape of the surgical landmark.

Any of the aspects herein, wherein the memory stores further data for processing by the processor that, when processed, causes the processor to: detect movement of the surgical landmark.

Any of the aspects herein, wherein the memory stores further data for processing by the processor that, when processed, causes the processor to: update a presentation of the virtual guide based on the movement of the surgical landmark; and cause the display to present the updated virtual guide within the augmented image.

Any of the aspects herein, wherein the memory stores further data for processing by the processor that, when processed, causes the processor to: generate a notification when the surgical landmark meets or exceeds one or more thresholds during the detected movement.

Any of the aspects herein, wherein the memory stores further data for processing by the processor that, when processed, causes the processor to: receive a surgical plan comprising one or more expected thresholds; and update the one or more expected thresholds based on the detected movement.

Any of the aspects herein, wherein the one or more expected thresholds comprises at least one of a force threshold, a positional threshold, a pressure threshold, an orientation threshold, and an acceleration threshold.

Any of the aspects herein, wherein determining the parameter is based on at least one of the one or more expected parameters, a surgical landmark within a field of view of the display, and a surgical step to be performed.

Any of the aspects herein, wherein the display comprises a headset.

Any of the aspects herein, wherein the surgical landmark comprises a plurality of vertebrae and the surgical plan comprises one or more surgical steps for moving the plurality of vertebrae to a predetermined alignment.

A system for performing a surgical procedure using a virtual guide according to at least one embodiment of the present disclosure comprises a display configured to display an augmented image in an environment; a processor; and a memory storing data for processing by the processor, the data, when processed, causes the processor to: detect a first surgical landmark in the environment and within a first field of view of the display; determine a first parameter of the first surgical landmark; generate a first virtual guide based on the first parameter of the first surgical landmark; detect a second surgical landmark in the environment and within a second field of view of the display; determine a second parameter of the second surgical landmark; generate a second virtual guide based on the second parameter of the second surgical landmark; and cause the display to present the augmented image such that at least one of the first virtual guide is presented on the first surgical landmark, the second virtual guide is presented on the second surgical landmark, and the first virtual guide is presented on the first surgical landmark and the second virtual guide is presented on the second surgical landmark.

Any of the aspects herein, wherein the first field of view and the second field of view are at least partially overlapping.

Any of the aspects herein, wherein the display comprises a headset.

Any of the aspects herein, wherein each of the first surgical landmark and the second surgical landmark comprises at least one of an anatomical element, an implant, and a marker.

Any of the aspects herein, wherein each of the first parameter and the second parameter comprises at least one of an angle, a pose, a position, an orientation, a size, a trajectory, and a shape of the first surgical landmark and the second surgical landmark.

Any of the aspects herein, wherein the memory stores further data for processing by the processor that, when processed, causes the processor to: detect movement of at least one of the first surgical landmark and the second surgical landmark.

Any of the aspects herein, wherein the memory stores further data for processing by the processor that, when processed, causes the processor to: update a presentation of at least one the first virtual guide and the second virtual guide based on the movement of the first surgical landmark and/or the second surgical landmark; and cause the display to present the updated at least one of the first virtual guide and the second virtual guide within the augmented image.

A device for performing a surgical procedure using a virtual guide according to at least one embodiment of the present disclosure comprises a processor; and a memory storing data for processing by the processor, the data, when processed, causes the processor to: track a surgical landmark visible in a field of vision of a display configured to display an augmented image of an environment; determine a parameter of the surgical landmark; generate a virtual guide based on the parameter of the surgical landmark; and cause the display to present the virtual guide overlapping with the surgical landmark as part of the augmented image of the environment.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
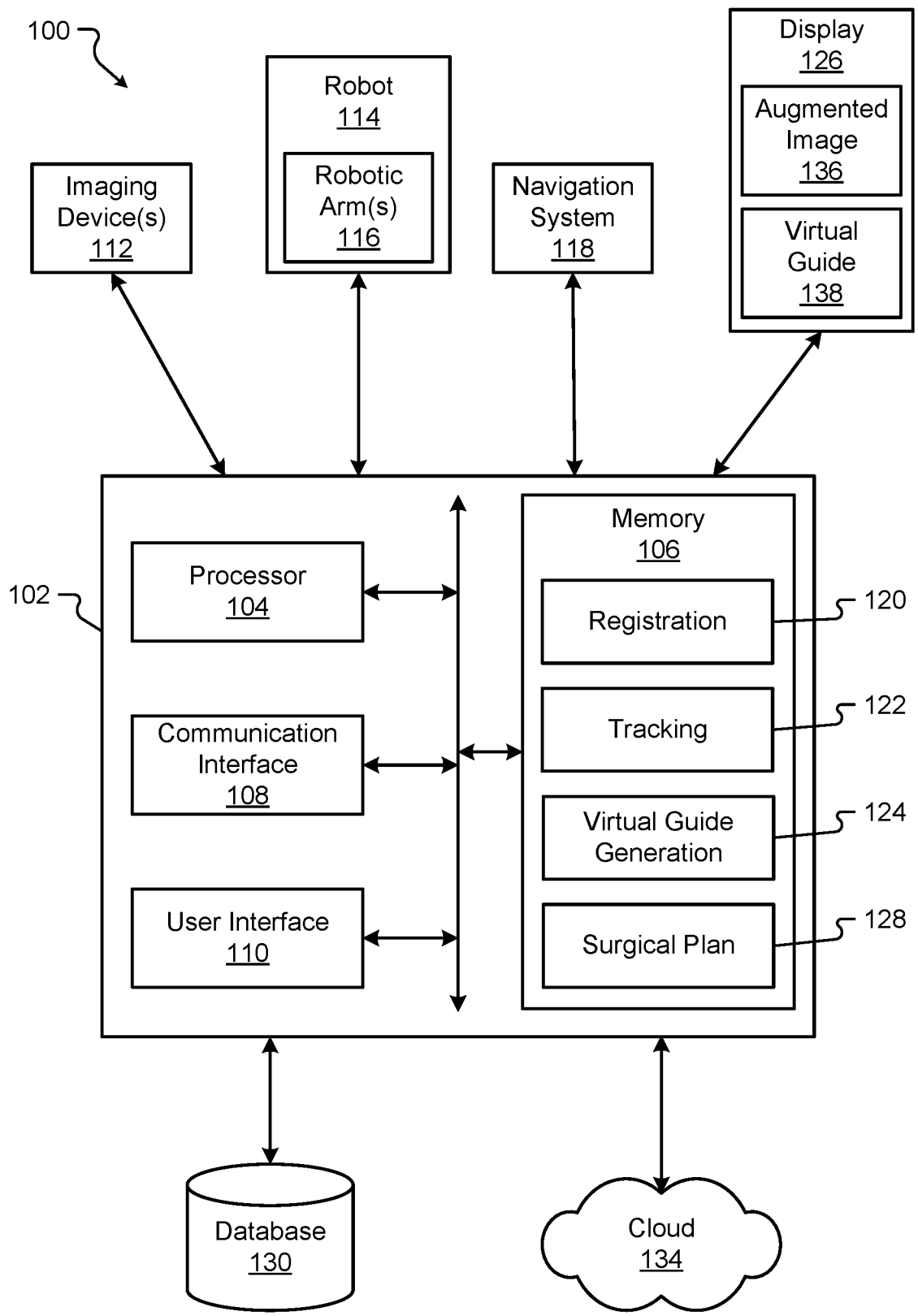
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

A patient may have a deformity such as a spinal deformity, which may be an abnormal alignment or curve of the bony vertebral column. Adult scoliosis and kyphosis can be caused by age-related wear and tear on the back and/or complications from past surgeries. A moderate deformity of a patient's spine may occur when the facet joints and discs deteriorate over time and are no long able to support the spine's normal posture. Pain may result from stressed joints and pinched nerves caused by the abnormal alignment. Conventional treatment may include medications, physical therapy, injections, or surgery.

Surgical options to correct a spinal deformity may vary depending on the severity of the symptoms, the number of spinal levels affected, and the type of deformity. A combination of different fusion and instrumentation techniques may be used to treat the patient's specific condition. Complex deformities such as, for example, kyphosis, often require the cutting of bone (osteotomy) and stabilization of the spine with long rods and screws in staged operations. The alignment is conventionally performed based on a surgeon's perception of the alignment without any substantial feedback as to whether the alignment was performed properly.

In at least one embodiment of the present disclosure, an augmented reality display is used to guide a surgeon on a surgical procedure such as a spinal alignment and provides the surgeon with virtual guides such as virtual lines and angles on top of the anatomy when the patient is lying on a surgery table. By seeing the virtual guides, the surgeon can use the additional information to perform the alignment safely and accurately. In addition to virtual guides such as virtual lines and angles, virtual recommendations may be provided for the execution of the procedure itself to minimize forces and pressures applied on the spine. Such embodiments provide crucial information to the surgeon to increase an accuracy of the procedure during the procedure and to reduce the surgeon's uncertainty of whether the procedure was performed accurately.

Embodiments of the present disclosure provide technical solutions to one or more of the problems of (1) providing virtual information about one or more anatomical elements during a surgical procedure, (2) effectively displaying virtual information during a surgical procedure, and (3) increasing an accuracy and safety of a surgical procedure.

Turning first to FIG. 1, a block diagram of a system 100 according to at least one embodiment of the present disclosure is shown. The system 100 may be used to generate and present a virtual guide during a surgical procedure and/or carry out one or more other aspects of one or more of the methods disclosed herein. The system 100 comprises a computing device 102, one or more imaging devices 112, a robot 114, a navigation system 118, a display 126, a database 130, and/or a cloud or other network 134. Systems according to other embodiments of the present disclosure may comprise more or fewer components than the system 100. For example, the system 100 may not include the imaging device 112, the robot 114, the display 126, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the display 126, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, and/or 500 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable a registration 120, tracking 122, and/or virtual guide generation 124.

The registration 120 enables the processor 104 to register or correlate a patient coordinate space with, for example, a display coordinate space of the display 126. The registration 120 may also enable the processor 104 to register or correlate any coordinate space with another coordinate space (e.g., a patient coordinate space to a robotic coordinate space, the patient coordinate space to a navigation coordinate space, the robotic coordinate space to the navigation coordinate space, etc.). The registration 120 may also enable the processor 104 to perform more than one registration or correlation of coordinate spaces. For example, the patient coordinate space may be correlated or registered with the navigation coordinate space and the navigation coordinate space may be correlated or registered with the display coordinate space. The registration 120 may be based on, for example, information about a pose of a patient during a surgical procedure. The information may be obtained from an imaging device such as the imaging device 112, sensors, and/or tracking devices affixed or placed on the patient. The information may also be obtained from an accurate robotic arm such as the robotic arm 116 or a navigated probe touching one or more points on the patient to obtain the pose of each point on the patient.

The tracking 122 enables the processor 104 (or a processor of the navigation system 118) to detect and track one or more surgical landmarks of the registered patient. The surgical landmark may comprise, for example, a reference marker, an implant implanted on an anatomical element, an anatomical element, and/or any other landmark in any combination thereof. The tracking 122 may enable the processor 104 to detect the surgical landmark by, for example, using image processing to process an image received from, for example, an imaging device such as the imaging device 112 to detect the surgical landmark depicted in the image and/or by using the navigation system 118 to detect the surgical landmark. The tracking 122 may, for example, also enable the processor 104 to track the surgical landmark for movement by comparing the surgical landmark at a first time period and a second time period to determine if movement of the surgical landmark has occurred. In other embodiments, the tracking 122 may, for example, enable the processor 104 to compare a pose of the surgical landmark at a first time period and a second time period to determine a change in the pose (and thus, movement of the surgical landmark).

The virtual guide generation 124 enables the processor 104 to generate a virtual guide 138 corresponding to a parameter associated with the surgical landmark. As will be described in more detail in FIG. 2, the parameter may comprise at least one of an angle, a pose, a position, an orientation, a size, a trajectory, and/or a shape of the surgical landmark. As will also be described in more detail below, the virtual guide 138 may be a visual aid to visualize the parameter. For example, an angle of a vertebra may be represented by a virtual line or rod extending from one end of the vertebra to another end of the vertebra and may include a number indicating the value of the angle. In such examples, the angle may be relative to, for example, an axis extending across a pelvic bone or shoulders of a patient. In some embodiments, the processor 104 may simply retrieve a corresponding virtual guide 138 from, for example, the memory 106, the database 130, or any other component in which the virtual guide 138 may be stored within. In other embodiments, the processor 104 may also automatically generate the virtual guide 138 based on preexisting or historical virtual guides 138 and historical parameters.

The content stored in the memory 106, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, the display 126, and/or the cloud 134.

The memory 106 may also store a surgical plan 128. The surgical plan 128 may comprise, for example, one or more steps for performing a surgical procedure and/or one or more expected thresholds for monitoring one or more parameters during the surgical procedure. In some embodiments, the surgical procedure may be a spinal procedure (e.g., a spinal alignment, installing implants, osteotomy, fusion, and/or any other spinal procedure) to correct a spinal deformity. For example, the surgical plan 128 may comprise one or more surgical steps for moving a plurality of vertebrae to a predetermined alignment. In such embodiments, the surgical landmark may comprise the plurality of vertebrae and the surgical plan 128 may include, for example, desired angles for one or more vertebrae, a desired shape of a patient's spine, and/or maximum force thresholds for an anatomical element such as, for example, a nerve. The surgical plan 128 may also be stored in the database 130.

The computing device 102 may also comprise a communication interface 108. The communication interface 108 may be used for receiving image data or other information from an external source (such as the imaging device 112, the robot 114, the navigation system 118, the database 130, the display 126, the cloud 134, and/or any other system or component not part of the system 100), and/or for transmitting instructions, images, or other information to an external system or device (e.g., another computing device 102, the imaging device 112, the robot 114, the navigation system 118, the database 130, the display 126, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The system 100 may also comprise the display 126. The display 126 may communicate with the computing device 102 or the processor 104 of the computing device to receive and present a virtual guide 138. It will be appreciated that in some embodiments, the display 126 can communicate with any component of the system 100 or any component external to the system 100. In some embodiments, the display 126 is an augmented display configured to display an augmented image 136 in which an environment is visible through at least a portion of the display 126 and the virtual guide 138 may be presented within the augmented image 136. In some embodiments, the virtual guide 138 may be visible as an overlay on the environment. In such embodiments, the display 126 may comprise a headset worn by a user. The headset may comprise a screen through which the environment is visible to the user and on which the virtual guide 138 may be displayed on. In some embodiments, the headset may display at least one virtual guide 138 corresponding to an object, anatomical element, portion of a patient, tool, and/or an instrument in a field of view of the headset. The headset may be beneficial in, for example, providing information to a user such as a surgeon during a surgical procedure. For example, the headset may display a presentation of one or more virtual guide(s) 138 corresponding to one or more surgical landmarks visible through the display 126. In such examples, the presentation of the virtual guide 138 may be updated as the surgical procedure progresses.

The augmented image 136 comprises one or more virtual representations that are visible to a user when presented in the display 126. The augmented image 136 (and thus, the virtual representation(s)) may appear as an overlay on the environment. Each virtual representation may appear as semi-transparent or opaque in the environment. The virtual representation may be two-dimensional or three-dimensional. The virtual representation may comprise, for example, the virtual guide 138. The augmented image 136 may comprise a first virtual guide 138 in a first field of view of the display 126 and a second virtual guide 138 in a second field of view of the display 126. In other words, the augmented image 136 may comprise different virtual guides 138 based on the field of view of the display 126. For example, the corresponding virtual guides 138 may change as the display 126 moves and views different portions of the environment.

The virtual guide 138 may be based on, for example, a parameter of a corresponding surgical landmark. The parameter may comprise, for example, an angle, a pose, a position, an orientation, a size, a trajectory, and/or a shape of the surgical landmark. For example, the parameter may comprise an angle, the surgical landmark may comprise a vertebra, and the virtual guide 138 may comprise a virtual line representing the angle of the vertebra overlaid onto the vertebra. In some embodiments, the virtual guide 128 may be a three-dimensional model of the surgical landmark. For example, image data may be received from the imaging device 112, as described below, and used to generate a three-dimensional model of the surgical landmark (which may be, for example, an anatomical element). The three-dimensional model may be updated to show changes to the surgical landmark(s), which may be advantageous when, for example, the entire surgical landmark is not visible. In other examples, the three-dimensional model may be used to visualize a global change. For example, a three-dimensional model of a spine may be updated to reflect changes resulting from movement of a vertebra.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, the display 126, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans 128 (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 200, 300, 400, and/or 500 described herein. The system 100 or similar systems may also be used for other purposes.

Figure 2:
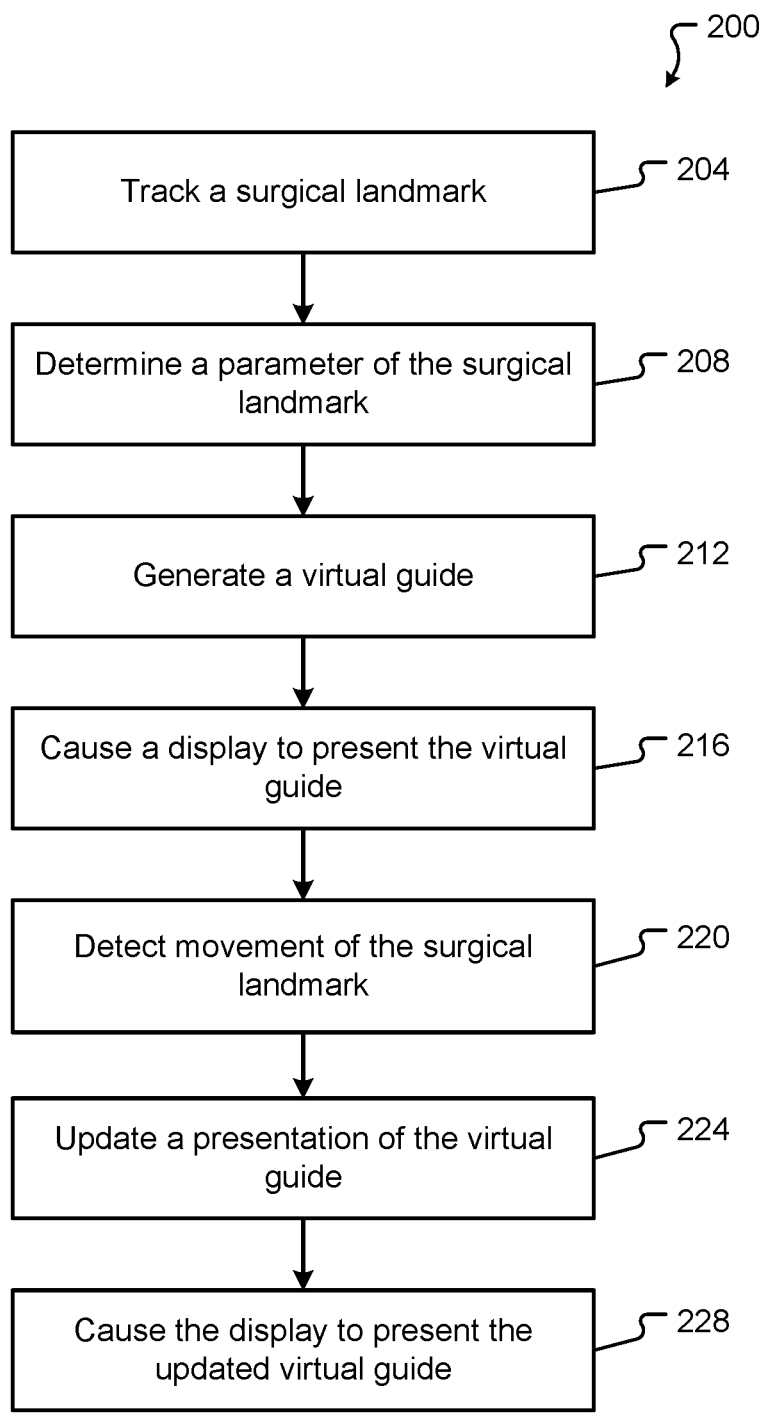
FIG. 2 is a flowchart according to at least one embodiment of the present disclosure.

FIG. 2 depicts a method 200 that may be used, for example, for generating and presenting a virtual guide during a surgical procedure.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing elements stored in a memory such as the memory 106. The elements stored in the memory and executed by the processor may cause the processor to execute one or more steps of a function as shown in method 200. One or more portions of a method 200 may be performed by the processor executing any of the contents of memory, such as a registration 120, tracking 122, and/or virtual guide generation 124.

The method 200 comprises tracking a surgical landmark (step 204). The surgical landmark may comprise, for example, a reference marker, an implant implanted on an anatomical element, an anatomical element, and/or any other landmark in any combination thereof. Tracking the surgical landmark may comprise a processor such as the processor 104 using a tracking such as the tracking 122 to detect and track the surgical landmark. The tracking may enable the processor to detect the surgical landmark in a field of view of, for example, a display such as the display 126. The surgical landmark may be detected by, for example, using image processing to process an image to identify the surgical landmark in the image and/or by using a navigation system such as the navigation system 118 to identify the surgical landmark.

The tracking may also enable the processor to detect track and movement of the surgical landmark by comparing the surgical landmark at a first time period and a second time period to determine if movement of the surgical landmark has occurred. In other embodiments, the tracking may, for example, enable the processor to compare a pose of the surgical landmark (whether determined from an image received from an imaging device such as the imaging device 112, receiving pose information about a reference marker tracked by a navigation system such as the navigation system 118, receiving pose information from a robotic arm such as the robotic arm 116 supporting or in contact with the surgical landmark, or otherwise) at a first time period and a second time period to determine a change in the pose (and thus, movement of the surgical landmark).

The method 200 also comprises determining a parameter of the surgical landmark (step 208). The parameter may be a feature of the surgical landmark. For example, the parameter may comprise an angle, a pose, a position, an orientation, a size, a trajectory, and/or a shape of the surgical landmark. Determining the parameter may be based on at least one factor. The at least one factor may comprise, for example, a step of a surgical procedure about to be performed or is being performed, a surgical landmark within a field of view of a display, and/or input from a user such as a surgeon or other medical provider. Some parameter(s) may provide desirable information to the user prior to or during the step of the surgical procedure. For example, an orientation and/or a position of one or more vertebrae may be helpful to view during tightening of one or more screws onto a rod to view. In another example, it may be desirable to monitor the change in orientation and/or position of the one or more vertebrae. In other instances, the user may select parameters that the user desires to view during a surgical step or surgical procedure.

The method 200 also comprises generating a virtual guide (step 212). The virtual guide may be the same as or similar to the virtual guide 138. Generating the virtual guide may comprise the processor using a virtual guide generation such as the virtual guide generation 124 to generate the virtual guide. Generating the virtual guide may be based on, for example, the parameter determined in step 208. In other instances, generating the virtual guide may be based on input received from a user such as a surgeon or other medical personnel. The processor may simply retrieve a corresponding virtual guide from, for example, a memory such as the memory 106, a database such as the database 130, or any other component in which the virtual guide may be stored within. In other instances, the processor may also automatically generate the virtual guide based on preexisting or historical virtual guides and historical parameters.

In some embodiments, the virtual guide may be a guide to visually display the parameter such as, for example, an angle of a surgical landmark or a position and/or orientation of the surgical landmark. For example, the virtual guide may comprise a virtual line or rod to visually show the angle of the surgical landmark. In other embodiments, the virtual guide may be predetermined based on, for example, a surgical plan such as the surgical plan 128. For example, the virtual guide may comprise text regarding a step in the surgical plan. In still other examples, the virtual guide may comprise a numerical coordinate of the surgical landmark. In other embodiments, the virtual guide may be related to minimizing at least one of a force and/or pressure applied to the surgical landmark. For example, the virtual guide may show a force and/or pressure applied to the surgical landmark by, for example, a robotic arm such as the robotic arm 116. Such force and/or pressure may be monitored by the user to prevent damage to the surgical landmark.

The method 200 also comprises causing a display to present the virtual guide (step 216). The virtual guide may be received from the step 212. In other instances, the virtual guide may be received from, for example, a database such as the database 130 or any other component. The display may be the same as or similar to the display 126 and may be configured to display an augmented image such as the augmented image 136. The display may be configured to present the virtual guide in the augmented image. In some embodiments, an environment is visible through the display and one or more surgical landmarks may be visible in the environment. In some embodiments, a display coordinate system of the display may be correlated or registered with a patient coordinate space by a processor such as the processor 104 using a registration such as the registration 120. In other embodiments, the display coordinate system may be correlated or registered with a navigation coordinate system of a navigation system such as the navigation system 118, which may be correlated or registered with a patient coordinate space. Such registration may enable the processor to detect which surgical landmarks are visible within the environment and a field of view of the display.

In some embodiments, the virtual guide may be displayed as an overlay on the environment visible in the display. The virtual guide may be displayed as opaque or semi-transparent and may be two-dimensional or three-dimensional. In some embodiments, the virtual guide may be displayed on a corresponding surgical landmark detected within the field of view of the display. For example, a virtual guide representing an angle of a vertebrae visible in the display may be displayed on the vertebrae. In such embodiments, and as will be explained in detail in FIGS. 3 and 4, different virtual guide(s) and/or multiple virtual guide(s) may be presented based on a corresponding surgical landmark visible in a field of view of the display. In other embodiments, the virtual guide may be displayed anywhere in the augmented image and may remain visible regardless of a field of view of the display.

It will be appreciated that more than one virtual guide may be presented at a time. For example, the display may present a virtual guide corresponding to and overlaid on the surgical landmark and another virtual guide displaying other information positioned anywhere in the augmented image. It will also be appreciated that more than one virtual guide may be presented for a corresponding surgical landmark. For example, a virtual line or rod representing an angle of the surgical landmark and a label identifying the surgical landmark may be presented on the surgical landmark.

The method 200 also comprises detecting movement of the surgical landmark (step 220). Detecting movement of the surgical landmark may be based on a comparison of a first image with a second image. The first image and the second image may be obtained from one or more imaging devices such as the imaging devices 112. More specifically, detecting the movement may comprise comparing a position of the surgical landmark in the first image to the position of the surgical landmark in the second image. In some embodiments, detecting movement of the at least one surgical landmark may comprise superimposing the second image over the first image and comparing differences between the surgical landmark depicted in the first image and the second image. The differences may be determined by visually detecting the differences between the first image and the second image. In other instances, the differences may be determined automatically by, for example, a processor such as the processor 104. For example, the processor may compare each pixel of the first image to each corresponding pixel of the second image and differences in pixels may indicate a difference between the first image and the second image.

In other embodiments, detecting the movement of the surgical landmark may be based on a comparison of pose information of the surgical landmark at a first timestamp and pose information of the surgical landmark at a second landmark. The pose information may be obtained from, for example, a navigation system such as the navigation system 118 tracking the surgical landmark, the navigation system tracking a marker affixed to the surgical landmark, a sensor disposed on the surgical landmark, a robotic arm such as the robotic arm 116 or a navigated probe touching the surgical landmark, and/or the robotic arm supporting the surgical landmark. A change in the pose information between the first timestamp and the second timestamp may indicate movement of the surgical landmark.

The method 200 also comprises updating a presentation of the virtual guide (step 224). The presentation of the virtual guide may be updated based on the movement detected in step 220. Updating the presentation of the virtual guide may comprise regenerating the virtual guide by, for example, repeating step 212. In other instances, updating the presentation of the virtual guide may comprise adjusting corresponding pixels of the virtual guide to reflect a change in the virtual guide based on the movement of the surgical landmark. For example, if the surgical landmark has tilted and the virtual guide is a virtual line or rod representing an angle of the surgical landmark, then the virtual line or rod may be tilted to match a new angle of the surgical landmark. In other examples, the virtual guide may be a representation of a spine of a patient the movement detected may be a vertebra that has moved or multiple vertebrae that have moved. In such examples, the representation of the spine may be updated to reflect the movement of the vertebrae (and may, in some instances, update one or more adjacent vertebra that may have moved as a result of the movement of the vertebrae).

The method 200 also comprises causing the display to present the updated virtual guide (step 228). The step 228 may be the same as or similar to the step 216 described above and with respect to presenting the updated virtual guide.

It will be appreciated that the steps 220-228 may be repeated continuously. In some embodiments, the virtual guide may be updated in real-time. In other embodiments, the steps 220-228 may be repeated incrementally or after a surgical step to view the updated virtual guide resulting from the surgical step.

The present disclosure encompasses embodiments of the method 200 that comprise more or fewer steps than those described above, and/or one or more steps that are different than the steps described above.

Figure 3:
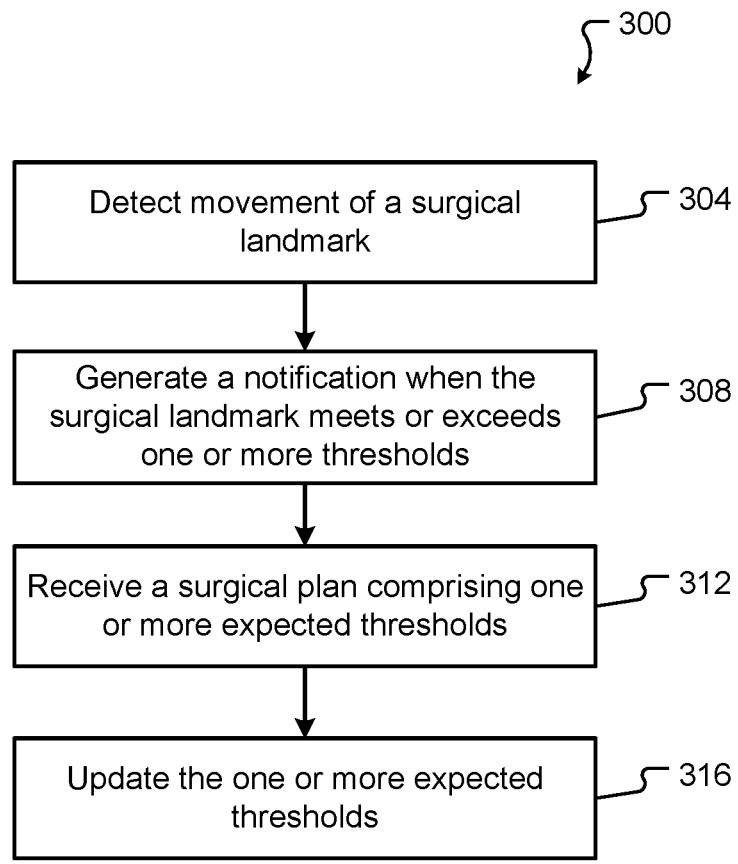
FIG. 3 is a flowchart according to at least one embodiment of the present disclosure.

FIG. 3 depicts a method 300 that may be used, for example, for generating a notification or updating one or more expected thresholds based on a detected movement of a surgical landmark.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of a method 300 may be performed by the processor executing any of the contents of memory, such as a registration 120, tracking 122, and/or virtual guide generation 124.

The method 300 comprises detecting movement of a surgical landmark (step 304). The step 304 may be the same as or similar to the step 220 of the method 200 described above.

The method 300 also comprises generating a notification when the surgical landmark meets or exceeds one or more thresholds (step 308). The notification may be a visual notification, an audible notification, or any type of notification communicated to a user. The notification may be communicated to the user via a user interface such as the user interface 110 or in the display. In some embodiments, the notification may be automatically generated by the processor 104. In other embodiments, the notification may be automatically generated by any component of a system such as the system 100.

The one or more thresholds may comprise, for example, a force threshold, a positional threshold, a pressure threshold, an orientation threshold, and/or an acceleration threshold. The one or more thresholds may be beneficial to monitor a surgical step and to, for example, prevent excessive force or pressure from being applied to an anatomical element or to ensure that an anatomical element has not moved outside of a desired range of movement. The one or more thresholds may be received as input from a user such as a surgeon or other medical provider. In other instances, the one or more thresholds may be based on the parameters determined in, for example, the step 208 of the method 200 above and/or received from a surgical plan such as the surgical plan 128. In such embodiments, the one or more thresholds may be generated automatically by a processor such as the processor 104 based on historical thresholds and historical parameters.

The method 300 also comprises receiving a surgical plan comprising one or more expected thresholds (step 312). The surgical plan may be the same as or similar to the surgical plan 128. The one or more thresholds described in step 308 above may be defined by the one or more expected thresholds provided in the surgical plan. The one or more expected thresholds may be received as input from a user such as a surgeon or other medical provider. In other embodiments, the one or more thresholds may be generated automatically by a processor such as the processor 104 based on historical thresholds and historical parameters.

The method 300 also comprises updating the one or more expected thresholds (step 316). The one or more expected thresholds may be updated, for example, in real-time prior to a start of or during a surgical procedure. For example, the one or more expected thresholds may have been generated based on one or more expected parameters. In such embodiments, prior to a start of the surgical procedure, or during the surgical procedure, actual parameters may be obtained. The actual parameters may be used to regenerate or update the expected thresholds.

The present disclosure encompasses embodiments of the method 300 that comprise more or fewer steps than those described above, and/or one or more steps that are different than the steps described above.

Figure 4:
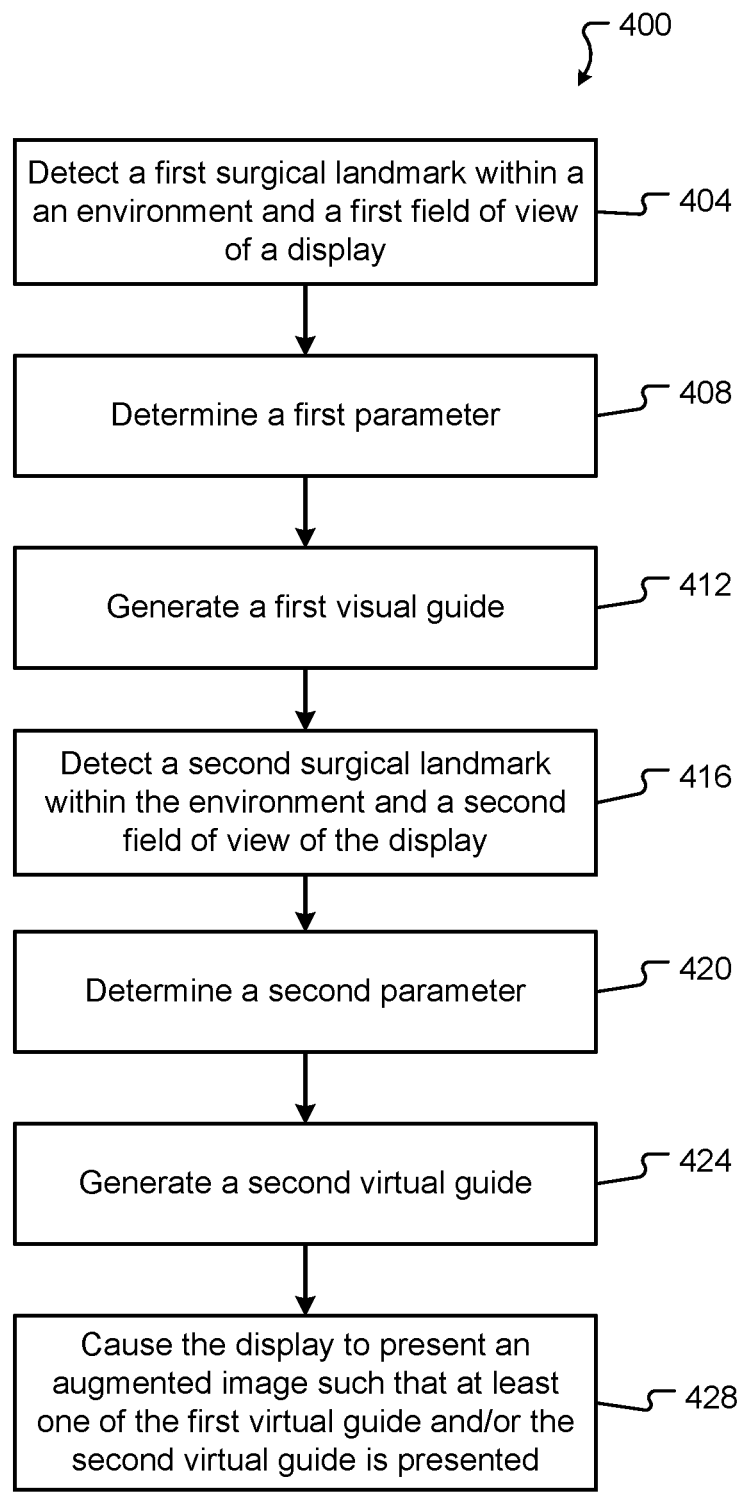
FIG. 4 is a flowchart according to at least one embodiment of the present disclosure.

FIG. 4 depicts a method 400 that may be used, for example, for generating and displaying a presentation of a virtual guide during a surgical procedure.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as a registration 120, tracking 122, and/or virtual guide generation 124.

The method 400 comprises detecting a first surgical landmark within an environment and a first field of view of a display (step 404). The display may be the same as or similar to the display 126. The environment may be visible through the display. In some embodiments, the environment is a surgical site. The first surgical landmark may comprise, for example, a reference marker, an implant implanted on an anatomical element, an anatomical element, and/or any other landmark in any combination thereof. Detecting the first surgical landmark may comprise a processor such as the processor 104 using a tracking such as the tracking 122 to detect and track the first surgical landmark. The tracking may, for example, enable the processor to detect the first surgical landmark in a first field of view of the display. The first surgical landmark may be detected by, for example, using image processing to process an image to identify the landmark in the image and/or by using a navigation system such as the navigation system 118 to identify the surgical landmark.

The method 400 also comprises determining a first parameter (step 408). The step 408 is the same as or similar to the step 208 of the method 200 above.

The method 400 also comprises generating a first visual guide (step 412). The step 412 is the same as or similar to the step 212 of the method 200 above.

The method 400 also comprises detecting a second surgical landmark within the environment and a second field of view of the display (step 416). The step 416 may be the same as or similar to the step 416 with respect to detecting the second surgical landmark within the second field of view. The second field of view may be the same as, overlap, or not overlap the first field of view. In other words, in some embodiments the first surgical landmark is visible at the same time as the second surgical landmark. In other embodiments, the display may move and the first surgical landmark may still be visible at the same time as the second surgical landmark. In still other embodiments, the display may move such that the first surgical landmark is not visible and the second surgical landmark is visible.

The method 400 also comprises determining a second parameter (step 420). The step 420 is the same as or similar to the step 208 of the method 200 above. The second parameter may be the same as the first parameter. For example, the first parameter may be a first angle for a first vertebrae and the second parameter may be a second angle for a second vertebrae. In other instances, the second parameter may be different from the first parameter. For example, the first parameter may be an angle for a first vertebra and the second parameter may be a pose of a second vertebra.

The method 400 also comprises generating a second virtual guide (step 424). The step 424 is the same as or similar to the step 212 of the method 200 above. The second virtual guide may be the same as the first virtual guide. For example, the first virtual guide may be a first rod representing a first angle for a first vertebrae and the second virtual guide may be a second rod representing a second angle for a second vertebrae. In other instances, the second virtual guide may be different from the first virtual guide. For example, the first virtual guide may be a rod representing an angle for a first vertebra and the second virtual guide may be a set of coordinates representing a pose of a second vertebra.

The method 400 also comprises causing the display to present an augmented image such that at least one of the first virtual guide and/or the second virtual guide is presented (step 428). The step 428 is the same as or similar to the step 216 of the method 200 above. In some embodiments, the first virtual guide is presented on the first surgical landmark when the first field of view is visible through the display and the second virtual guide is presented on the second surgical landmark with the second field of view is visible through the display. In other embodiments, the first virtual guide is presented on the first surgical landmark and the second virtual guide is presented on the second surgical landmark when the first field of view and the second field of view are the same or overlapping. In other words, as the display moves and the field of view changes, one or more surgical landmarks (whether the first surgical landmark and/or the second surgical landmark) are detected and the corresponding virtual guide is presented.

It will be appreciated that one, two, or more than two surgical landmarks may be detected and one, two, or more than two corresponding visual guides may be generated. In other words, any number of surgical landmarks may be detected, any number of corresponding visual guides may be generated, and any number of visual guides may be presented by the display.

The present disclosure encompasses embodiments of the method 400 that comprise more or fewer steps than those described above, and/or one or more steps that are different than the steps described above.

Figure 5:
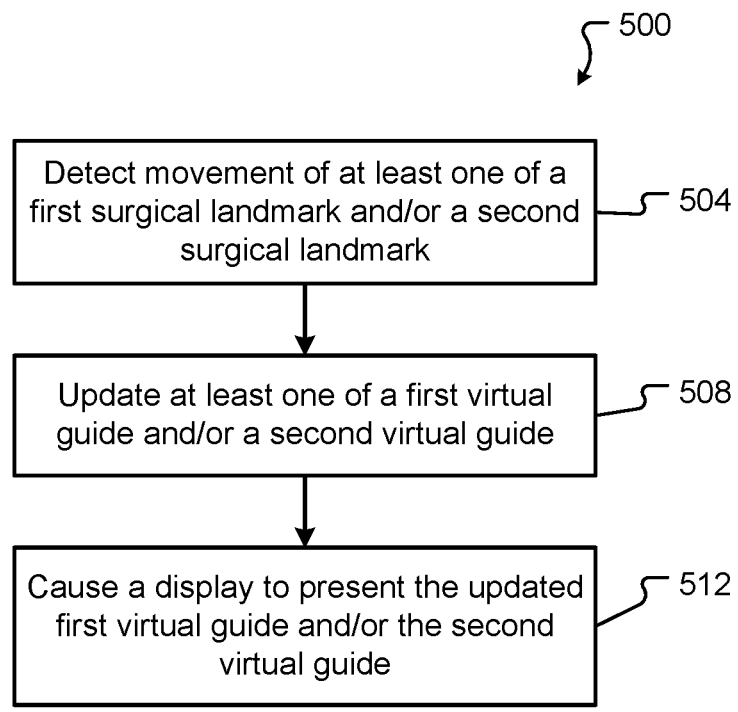
FIG. 5 is a flowchart according to at least one embodiment of the present disclosure.

FIG. 5 depicts a method 500 that may be used, for example, for updating one or more virtual guides based on a detected movement of one or more surgical landmarks.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing elements stored in a memory such as the memory 106. The elements stored in memory and executed by the processor may cause the processor to execute one or more steps of a function as shown in method 500. One or more portions of a method 500 may be performed by the processor executing any of the contents of memory, such as a registration 120, tracking 122, and/or virtual guide generation 124.

The method 500 comprises detecting movement of at least one of a first surgical landmark and/or a second surgical landmark (step 504). The step 504 may be the same as or similar to the step 220 of the method 200 described above. In some embodiments, the first surgical landmark may be visible within the same field of view as the second surgical landmark. In other embodiments, the first surgical landmark may not be visible at the same time as the second surgical landmark.

The method 500 also comprises updating at least one of a first virtual guide and/or a second virtual guide (step 508). The step 508 may be the same as or similar to the step 224 of the method 200 described above. The first virtual guide and/or the second virtual guide may be received from the steps 412 and 424 of the method 400 described above.

The method 500 also comprises causing a display to present the updated first virtual guide and/or the second virtual guide (step 512). The step 512 may be the same as or similar to the step 228 of the method 200 described above.

It will be appreciated that the steps 504-512 may be repeated continuously. In some embodiments, the first virtual guide, the second virtual guide, or any virtual guide may be updated in real-time. In other embodiments, the steps 504-512 may be repeated incrementally or after a surgical step to view the updated virtual guide resulting from the surgical step.

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 2, 3, 4, and 5 (and the corresponding description of the methods 200, 300, 400, and 500), as well as methods that include additional steps beyond those identified in FIGS. 2, 3, 4, and 5 (and the corresponding description of the methods 200, 300, 400, and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for performing a surgical procedure using a virtual guide, the system comprising:
a display configured to display an augmented image in an environment;
a processor; and
a memory storing data for processing by the processor, the data, when processed, causes the processor to:
track a first vertebra of a plurality of vertebrae;
determine an angle of the first vertebra of the plurality of vertebrae relative to a second vertebra of the plurality of vertebrae;
generate a first virtual guide for presentation within the augmented image that includes a first visual indicator of the angle of the first vertebra relative to the second vertebra, the first visual indicator comprising a virtual rod extending from one end of the first vertebra to another end of the first vertebra;
generate a second virtual guide for presentation within the augmented image that relates to at least one of a force and a pressure applied to the first vertebra;
generate a third virtual guide for presentation within the augmented image that includes text regarding a step in a surgical plan; and
cause the display to present the first virtual guide within the augmented image.

2. The system of claim 1, wherein the second virtual guide provides a second visual indicator related to at least one of the force and the pressure applied to the first vertebra.

3. The system of claim 1, wherein the memory stores further data for processing by the processor that, when processed, causes the processor to:
track at least one of an implant and a marker.

4. The system of claim 1, wherein the memory stores further data for processing by the processor that, when processed, causes the processor to:
determine at least one of a pose, a position, an orientation, a size, and a trajectory of the first vertebra.

5. The system of claim 1, wherein the memory stores further data for processing by the processor that, when processed, causes the processor to:
detect movement of the first vertebra.

6. The system of claim 5, wherein the memory stores further data for processing by the processor that, when processed, causes the processor to:
update a presentation of the first virtual guide based on the movement of the first vertebra; and
cause the display to present the updated first virtual guide within the augmented image.

7. The system of claim 5, wherein the memory stores further data for processing by the processor that, when processed, causes the processor to:

generate a notification when a parameter associated with the first vertebra meets or exceeds one or more threshold values during the detected movement.

8. The system of claim 7, wherein the memory stores further data for processing by the processor that, when processed, causes the processor to:
receive the surgical plan comprising one or more expected threshold values; and
update the one or more expected threshold values based on the detected movement.

9. The system of claim 8, wherein the one or more expected threshold values comprises at least one of a force threshold value, a positional threshold value, a pressure threshold value, an orientation threshold value, and an acceleration threshold value.

10. The system of claim 1, wherein determining the angle of the first vertebra relative to the second vertebra is based on at least one of one or more expected parameters, a surgical landmark within a field of view of the display, and a surgical step to be performed.

11. The system of claim 1, wherein the display comprises a headset.

12. The system of claim 1, wherein a surgical plan comprises one or more surgical steps for moving the plurality of vertebrae to a predetermined alignment.

13. A system for performing a surgical procedure using a virtual guide comprising:
a display configured to display an augmented image in an environment;
a processor; and
a memory storing data for processing by the processor, the data, when processed, causes the processor to:
detect a first vertebra in the environment and within a first field of view of the display;
determine at least one of a force and a pressure applied to the first vertebra;
generate a first virtual guide for presentation within the augmented image based on at least one of the force and the pressure applied to the first vertebra;
detect a second vertebra in the environment and within a second field of view of the display;
determine an angle of the second vertebra relative to the first vertebra;
generate a second virtual guide for presentation within the augmented image that includes a visual indicator of the angle of the second vertebra relative to the first vertebra, the visual indicator comprising a virtual rod extending from one end of the first vertebra to another end of the second vertebra;
generate a third virtual guide for presentation within the augmented image that includes text regarding a step in a surgical plan; and
cause the display to present the first virtual guide, the second virtual guide, and the third virtual guide within the augmented image.

14. The system of claim 13, wherein the first field of view and the second field of view are at least partially overlapping.

15. The system of claim 13, wherein the display comprises a headset.

16. The system of claim 13, wherein the memory stores further data for processing by the processor that, when processed, causes the processor to:
detect at least one of an implant and a marker.

17. The system of claim 13, wherein the memory stores further data for processing by the processor that, when processed, causes the processor to:
determine, at least one of a pose, a position, an orientation, a size, and a trajectory the first vertebra and the second vertebra.

18. The system of claim 13, wherein the memory stores further data for processing by the processor that, when processed, causes the processor to:
detect movement of at least one of the first vertebra and the second vertebra.

19. The system of claim 18, wherein the memory stores further data for processing by the processor that, when processed, causes the processor to:
update a presentation of at least one the first virtual guide and the second virtual guide based on the movement of at least one of the first vertebra and the second vertebra; and
cause the display to present at least one of the updated first virtual guide and the updated second virtual guide within the augmented image.

20. A device for performing a surgical procedure using a virtual guide, the device comprising:
a processor; and
a memory storing data for processing by the processor, the data, when processed, causes the processor to:
track a first vertebra visible in a field of vision of a display configured to display an augmented image of an environment;
determine an angle of the first vertebra relative to a second vertebra;
generate a first virtual guide based on the angle of first vertebra relative to the second vertebra, the first virtual guide comprising a virtual rod extending from one end of the first vertebra to another end of the first vertebra;
generate a second virtual guide for presentation within the augmented image that relates to at least one of a force and a pressure applied to the first vertebra;
generate a third virtual guide for presentation within the augmented image that includes text regarding a step in a surgical plan; and
cause the display to present the first virtual guide overlapping with the first vertebra as part of the augmented image of the environment.

* * * * *